United States Patent
Payan et al.

(10) Patent No.: US 7,863,222 B2
(45) Date of Patent: Jan. 4, 2011

(54) SHRNA LIBRARY

(75) Inventors: Donald G. Payan, Hillsborough, CA (US); Mary Shen, Newark, CA (US); Simon Yu, Newark, CA (US); Todd M. Kinsella, Redwood City, CA (US); Yasumichi Hitoshi, Mountain View, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/221,325

(22) Filed: Aug. 1, 2008

(65) Prior Publication Data
US 2010/0029505 A1 Feb. 4, 2010

(51) Int. Cl.
C40B 50/06 (2006.01)
C40B 40/08 (2006.01)
C40B 30/06 (2006.01)
C40B 40/02 (2006.01)
C12P 19/34 (2006.01)
A61K 49/12 (2006.01)

(52) U.S. Cl. .......................... 506/26; 435/91.2; 506/17; 506/10

(58) Field of Classification Search ........................ None
See application file for complete search history.

(56) References Cited

U.S. PATENT DOCUMENTS

| 2005/0130184 A1 | 6/2005 | Xu et al. |
| 2005/0130919 A1 | 6/2005 | Xu et al. |
| 2007/0231807 A1 | 10/2007 | Mo |

FOREIGN PATENT DOCUMENTS

| WO | WO 2005/023991 A2 * | 3/2005 |
| WO | WO2005059157 A2 | 6/2005 |

OTHER PUBLICATIONS

Hutchison (PNAS, USA, 2005, vol. 102, p. 17332).*
Bittker (Apr. 26, 2004) PNAS USA vol. 101 p. 7011.*
Kodumal (Oct. 20, 2004) PNAS USA vol. 101 p. 15573.*
Hutchison (Nov. 25, 2005) PNAS USA vol. 102 p. 17332.*

(Continued)

*Primary Examiner*—Jeffrey S Lundgren
*Assistant Examiner*—Christian Boesen
(74) *Attorney, Agent, or Firm*—James S. Keddie; Travis Young; Bozicevic, Field & Francis LLP

(57) ABSTRACT

As noted above, certain aspects of this disclosure relate to a library of nucleic acid vectors, as well as a method for making the same. In certain embodiments, the library of nucleic acid vectors comprises: a plurality of nucleic acid molecules of the following formula: $S_1$—R—$S_2$ wherein, in each nucleic acid of the plurality: $S_1$ and $S_2$ are each at least 15 nucleotides in length; $S_1$ and $S_2$ are complementary to each other along their entire length; either $S_1$ or $S_2$ is complementary along its entire length to a sequence in eukaryotic mRNA; and R is a six base recognition site for a restriction endonuclease; and wherein $S_1$ and $S_2$ vary in nucleotide sequence between different members of the plurality. A method for amplifying a circular nucleic acid is also provided.

7 Claims, 14 Drawing Sheets
(2 of 14 Drawing Sheet(s) Filed in Color)

OTHER PUBLICATIONS

Li (Dec. 12, 2000) Theoretical and Applied Genetics vol. 101 p. 1259.*

Dean, F., et al. Rapid amplification of plasmid and phage DNA using Phi29 DNA polymerase and multiply-primed rolling circle amplification. Genome Research. 2001, vol. 11, pp. 1095-1099.

Dinh, A., et al. Alternative approach to generate shRNA from cDNA. BioTechniques. 2005, vol. 38, No. 4, pp. 629-632.

Luo, B., et al. Small interfering RNA production by enzymatic engineering of DNA (SPEED). PNAS. 2004, vol. 101, No. 15, pp. 5494-5499.

Sen, G., et al. Restriction enzyme-generated siRNA (REGS) vectors and libraries. Nature Genetics. 2004, vol. 36, No. 2, pp. 183-189.

Shirane, D., et al. Enzymatic production of RNAi libraries from cDNAs. Nature Genetics. 2004, vol. 36, No. 2, pp. 190-196.

* cited by examiner

Adaptor1 (pAd1-R14) 67 mer SEQ ID NO:1

5'- p-CTCGGCAATTCCGCCTCCAGTCAGATGAGAGACACACTCTCATCTGACTGGAG
GCGGAATTGCCGAG-3'

Adaptor 1 forms a hairpin as follows:

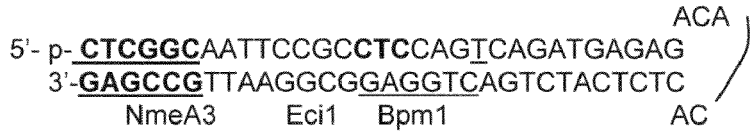

```
                                                    ACA  ⎞
 5'- p- CTCGGCAATTCCGCCTCCAGTCAGATGAGAG                  ⎟
    3'-GAGCCGTTAAGGCGGAGGTCAGTCTACTCTC                   ⎠
      NmeA3    Eci1    Bpm1                         AC
```

Adaptor2: (pAd2-R13) 24 mer SEQ ID NO:2

5'-p-GGATCCAATGCATGATGGATCC-NN-3'

Adaptor 2 forms a hairpin as follows:

```
              ATGC  ⎞
 5'-p-GGATCCA       ⎟
 3'-NNCCTAGGT       ⎠
              AGTA
```

Adaptor3 (pAD3-R13-10b) 42 mer SEQ ID NO:3

5'-p-AGATCGACTCTTCATCTGTCAGTTCATGAAGACTAGATCTNN-3'

Adaptor 3

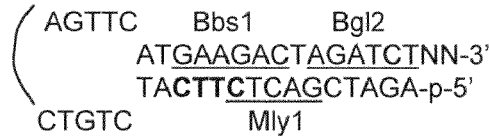

```
 ⎛ AGTTC    Bbs1      Bgl2
 ⎜     ATGAAGACTAGATCTNN-3'
 ⎝     TACTTCTCAGCTAGA-p-5'
  CTGTC        Mly1
``` ext- primers for amplification by phi29 polymerase and DNA polymerase1:

ext-R13-8R primer:    8 mer    5'-GAACTGAC-3' for single strand DNA synthesis ext-R13-10F primer:   8 mer    5'-CTTCATCT-3' for double strand DNA synthesis

Fig. 4

Step 1. ligation 1: B (blunted-ended DNA fragment) + (Y282-1) pAd1-R14:

(Y282-1) pAd1-R14: 67 mer PAGE ug/ul (SEQ ID NO:1)

(SEQ ID NO:7)

Fermentas Rapid Ligation Kit (#K1423)

| | |
|---|---|
| B end-DNA (B) (0.5 ug/ul) | 12 ul (6ug) |
| (Y282-1) pAd1-R14  1ug/ul | 7.2ul (7.2ug) |
| 5x DNA ligation buffer | 28 ul |
| T4 DNA ligase | 7 ul |
| H2O | 85.8 ul |
| total | 140 ul |

Room temp. 1h15'
+70ul H2O, phenol:chloroform extraction once, chloroform extraction once, then ethanol precipitation.

Fig. 5 page 1

Step 2. NmeA3 digestion:

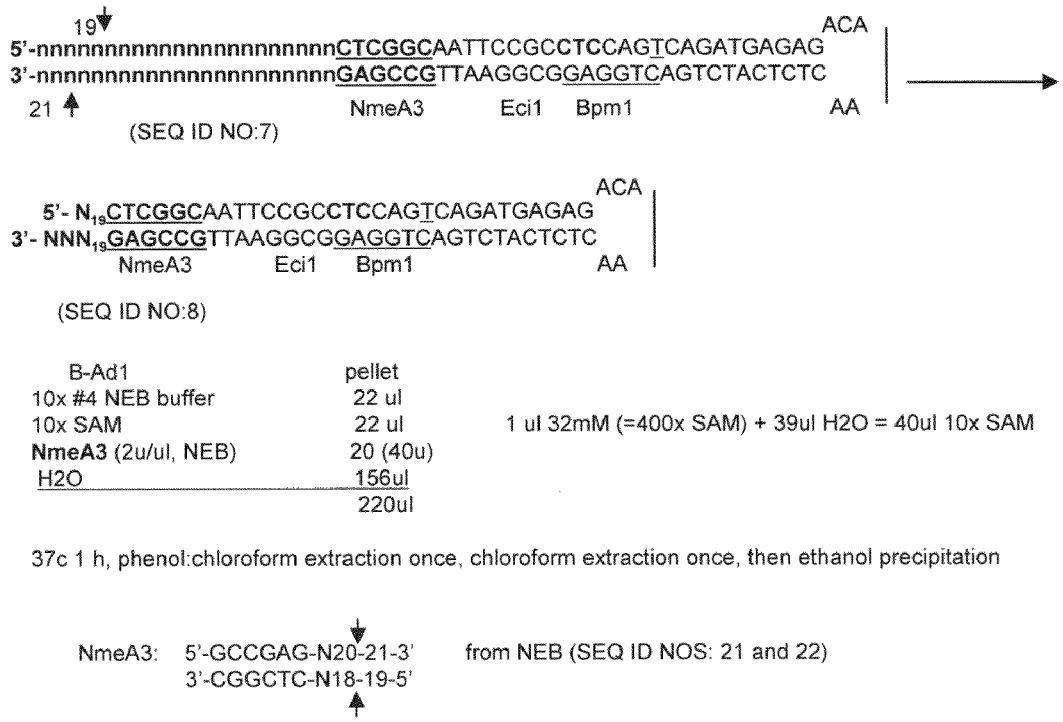

```
     19▼                                              ACA
5'-nnnnnnnnnnnnnnnnnnnnnnnCTCGGCAATTCCGCCTCCAGTCAGATGAGAG
3'-nnnnnnnnnnnnnnnnnnnnnnnGAGCCGTTAAGGCGGAGGTCAGTCTACTCTC
  21 ▲              NmeA3    Eci1    Bpm1            AA
         (SEQ ID NO:7)
```

```
                                                 ACA
5'- N₁₉CTCGGCAATTCCGCCTCCAGTCAGATGAGAG
3'- NNN₁₉GAGCCGTTAAGGCGGAGGTCAGTCTACTCTC
       NmeA3    Eci1    Bpm1            AA (SEQ ID NO:8)
```

| | |
|---|---|
| B-Ad1 | pellet |
| 10x #4 NEB buffer | 22 ul |
| 10x SAM | 22 ul |
| NmeA3 (2u/ul, NEB) | 20 (40u) |
| H2O | 156ul |
| | 220ul |

1 ul 32mM (=400x SAM) + 39ul H2O = 40ul 10x SAM 37c 1 h, phenol:chloroform extraction once, chloroform extraction once, then ethanol precipitation

```
              ▼
NmeA3:  5'-GCCGAG-N20-21-3'     from NEB (SEQ ID NOS: 21 and 22)
        3'-CGGCTC-N18-19-5'
              ▲
```

Fig. 5 page 2

Step 3. ligation 2: mB-Ad1 + (Y269-2) pAd3-R13-10b
(Y269-2) pAd3-R13-10b: 42mer Fermentas Rapid Ligation Kit (#K1423)

```
      nB-Ad1                         pellet
Y269-2 pAd3-R13-10b 1.3ug/ul)        5.6ul (7.2 ug)
5x DNA ligation buffer               28 ul
T4 DNA ligase                        7 ul
H2O                                  99.4ul
   total                             140 ul
```

Room Temp 1h, 65c 10'

Step 4. GP1: Ad3-B-Ad1 (75 bp)

| Ad1 | 34bp |
|---|---|
| Ad1-dimer | 67bp |
| nB-Ad1 | 55bp |
| nB-Ad1-dimer | 108bp |
| Ad3 | 22bp |
| Ad3-dimer | 42bp |
| Ad3-B-Ad1 | 75bp |

Fig. 5 page 3

Step 5. Bpm1, Bci1 digestion:

```
AGTTC    Bbs1      Bgl2                                              ACA
  | ATGAAGACTAGATCTNNN₁₉CTCGGCAATTCCGCCTCCAGTCAGATGAGAG |
  | TACTTCTCAGCTAGANNN₁₉GAGCCGTTAAGGCGGAGGTCAGTCTACTCTC |
CTGTC    Mly1              NmeA3      Eci1  Bpm1              AA
```
(SEQ ID NO:9)                                                                →

```
AGTTC    Bbs1      Bgl2                                              ACA
  | ATGAAGACTAGATCTNNN₁₉-3'         5'- CTCGGCAATTCCGCCTCCAGTCAGATGAGAG |
  | TACTTCTCAGCTAGAN₁₉-5'           3'-NNGAGCCGTTAAGGCGGAGGTCAGTCTACTCTC |
CTGTC    Mly1                              NmeA3      Eci1  Bpm1              AA
```
(SEQ ID NO:10)                              (SEQ ID NO:11)

Bpm1 digestion:

| Reaction | pellet |
|---|---|
| 10x #3 NEB buufer | 3 ul |
| 10x BSA | 3ul |
| Bpm1 (2.5u/ul NEB) x 2u/ug | 3 ul (7.5u) |
| H2O | 21 ul |
| Total | 30 ul |

37c 3 h,

| reaction | 30ul |
|---|---|
| 10x #2 buffer | 2.5ul |
| 10x BSA | 2.5 ul |
| Eci1 (2u/ul) | 2.5 ul (5u) |
| H2O | 17.5 ul |
| Total | 55 ul |

37c 3h

+110ul H2O phenol:chloroform extraction once, chloroform extraction once, then ethanol precipitation

Bpm1: 5'-CTGGAG-n16-3'   from NEB SEQ ID NOS 23 and 24
         3'-GACCTC-n14-5'
                       ↕
Eci1: 5'-GGCGGA-N11-3'   from NEB SEQ ID NOS 25 and 26
          3'-CCGCCT-N9 -5'
                       ↑

Fig. 5 page 4

Step 6. L3: + pAd2-R13 pAd2-R13: (Y252-5)

```
              ATGC|
5'-p-GGATCCA      |    (SEQ ID NO:2)
3'-NNCCTAGGT      |
              AGTA|
``` pAd2-R13:   24 mer   5'-p-<u>GGATCC</u>AATGCATGAT<u>GGATCC</u>-NN-3'   (SEQ ID NO:2)

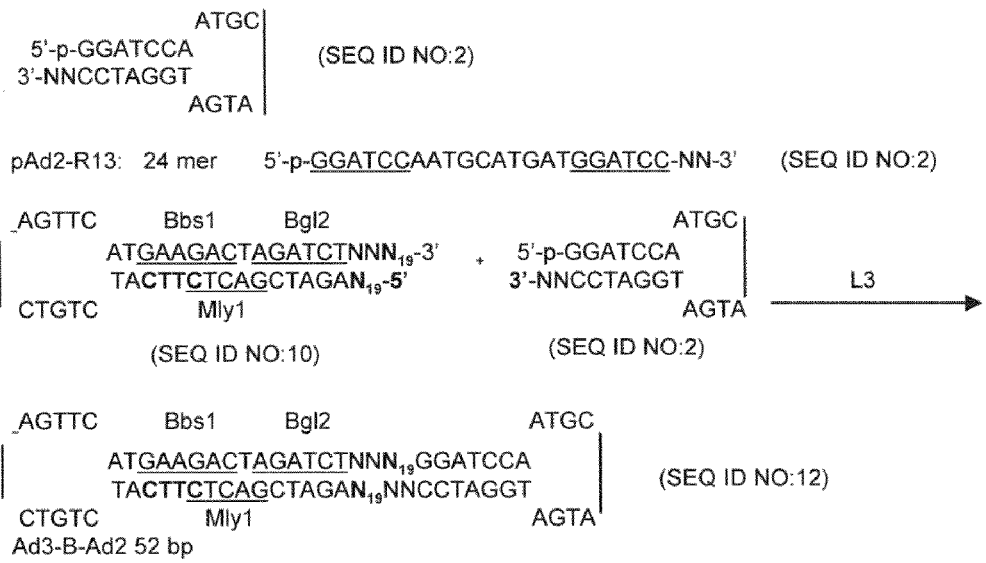

```
_AGTTC     Bbs1      Bgl2                               ATGC|
|    AT<u>GAAGAC</u>TAGATCTNNN₁₉GGATCCA                    |
|    TACT<u>TC</u>TCAGCTAGAN₁₉NNCCTAGGT                    |   (SEQ ID NO:12)
 CTGTC     Mly1                                     AGTA|
Ad3-B-Ad2 52 bp
```

Fermentas Rapid Ligation Kit (#K1423)

|  | B-Ad3 | pellet |
| --- | --- | --- |
| pAd2-R13: (Y252-5 1.48ug/ul) | | 1.35 ul (2 ug) |
| 5x DNA ligation buffer | | 10ul |
| T4 DNA ligase | | 2.5 |
| H2O | | 36.15 ul |
| total | | 50 ul |

Room Temp. 1h. 65c 10', ppt

| DNA | pellet (1ug) |
| --- | --- |
| 10x #3 NEB buufer | 3 ul |
| 10x BSA | 3ul |
| Bpm1 (2.5u/ul NEB) x 2u/ug | 3 ul (7.5u) |
| H2O | 21 ul |
| Total | 30 ul |

37c 3h

Step 7. GP2: to get Ad3-B-Ad2 52bp

| | |
| --- | --- |
| Ad3-Bp | 41bp |
| Ad3-Bp-dimer | 80bp |
| Ad3-B-Ad1 | 75bp |
| Ad1-p | 36bp |
| Ad1-p-Ad2 | 47bp |
| Ad1-p-dimer | 70bp |
| Ad2 | 13bp |
| Ad2-dimer | 24bp |
| Ad3-B-Ad2 | 52bp |

Fig. 5 page 5

Step 8. Amplification by Phi29 DNA polymerase:

```
AGTTC     Bbs1      Bgl2            ATGC
 |   ATGAAGACTAGATCTNNN₁₀GGATCCA       |
 |   TACTTCTCAGCTAGAN₁₀NNCCTAGGT       |
CTGTC     Mly1              AGTA
52 bp
          (SEQ ID NO:12)
```

```
 | TCAAGTACTTCTGATCTAGANNN₁₀CCTAGGTTACG  |
 | GACAGATGAAGAGTCGATCTN₁₀NNGGATCCATCAT  |       (SEQ ID NO:13)
```

| | |
|---|---|
| Ad3-B-Ad2 DNA | 10 ul |
| (Y279-1) ext-R13-8R | 1.4 ul |
| 10 x phi 29DNA polymerase buffer | 7 ul |
| 10 x BSA | 7 ul |
| 10mM dNTPea | 2.5 ul |
| 0.1 M DTT | 0.25 ul |
| phi29 DNA polymerase (10u/ul) | 1.4 ul |
| H2O | 40.55 ul |
| Total | 70 ul |

30c 15 h
67c 12'   +30ul H2O, 50ul 4M NH4oAc, 375ul EtOH, dryice 3', 16c spin 15' at 14K speed.

ext primers:  Y279-1  ext-R13-8R primer:  8 mer  5'-GAACTGAC-3' (SEQ ID NO 27)
              Y269-3  ext-R13-10F primer: 8 mer  5'-CTTCATCT-3' (SEQ ID NO 28)

Fig. 5 page 6

Step 9. 2nd strand synthesis by DNA Polymerase 1

| TCAAGTACTTCTGATCTAGANNN₁₉CCTAGGTTACG |
| GACAGATGAAGAGTCGATCTN₁₉NNGGATCCATCAT |
→ (Y269-3) ext-R13-10F (SEQ ID NO:13)

```
        Bbs1      Bgl2
AGTTCATGAAGACTAGATCTNNN₁₉GGATCCAATGC
TCAAGTACTTCTGATCTAGANNN₁₉CCTAGGTTACG

GACAGATGAAGAGTCGATCTN₁₉NNGGATCCATCAT
CTGTCTACTTCTCAGCTAGAN₁₉NNCCTAGGTAGTA    (SEQ ID NO:14)
```

```
        ssDNA                       pellet
(Y269-3)  ext-R13-10F                8 ul
        H2O                         49 ul
94c 3', dry ice 10x #2 NEB                          7.0 ul
10 mM dNTPea                        2.5 ul
Klenow (5u/ul, Roche)               0.5 ul
M0210L Klenow (5u/ul, NEB)          1.5 ul
M0209L DNA Polymerase 1 (10u/ul)    1.5 ul
Total                                70 ul
```

37c 1h. + 90 ul H2O, φ/c, c, ppt
Put on dryice 3', 16c spin 16' at 14K speed.
pellet in 30ul H2O

Fig. 5 page 7

Step 10. Bbs1/Mly1/Bgl2:

```
        Bbs1      Bgl2
AGTTCATGAAGACTAGATCTNNN₁₉GGATCCAATGC
TCAAGTACTTCTGATCTAGANNN₁₉CCTAGGTTACG                    (SEQ ID NO:14)

GACAGATGAAGAGTCGATCTN₁₉NNGGATCCATCAT
CTGTCTACTTCTCAGCTAGAN₁₉NNCCTAGGTAGTA
              Mly1
```

```
   Bbs1       Bgl2                                      Mly1
GAAGACTAGATCTNNN₁₉GGATCCAATGCATGATGGATCCNNN₁₉AGATCGACTC   (SEQ ID NO:14)
CTTCTGATCTAGANNN₁₉CCTAGGTTACGTACTACCTAGGN₁₉NNTCTAGCTGAG
```

Bbs1, Mly1, Bgl2 digestion:

```
              BamH1    Nsi1      BamH1
5'-GATCTNNN₁₉GGATCCAATGCATGATGGATCCNNN₁₉-3'   (SEQ ID NO:15)
3'-    ANNN₁₉CCTAGGTTACGTACTACCTAGGNNN₁₉-5'   (SEQ ID NO:16)
                        67 bp
```

Mly1 digestion

| | |
|---|---|
| 1st digested DNA | 10ul |
| 10 x #4 NEB | 7 ul |
| 10 x BSA | 7 ul |
| Mly1 (10u/ul) | 6 ul (50u) |
| H2O | 40 ul |
| Total | 70 ul |

37c >5h or O/N   ppt

Bgl2 digestion

| | |
|---|---|
| Ad3-B-Ad2 DNA | pellet (4ug) |
| 10 x #3 NEB | 7ul |
| Bgl2 (10u/ul) | 6ul (60u) |
| H2O | 57 ul |
| Total | 70 ul |

37c 3.5h
Ppt

Bbs1 digestion:

| | |
|---|---|
| DNA | pellet |
| 10x #2 | 6 ul |
| Bbs1 (5u/ul) | 6 (30u) |
| H2O | 48 |
| Total | 60 ul |

37c 3h

Fig. 5 page 8

Step 11. GP3 (GEL PURIFICATION): to get sh 67 bp

Step 12. ligate to RNAi vector:

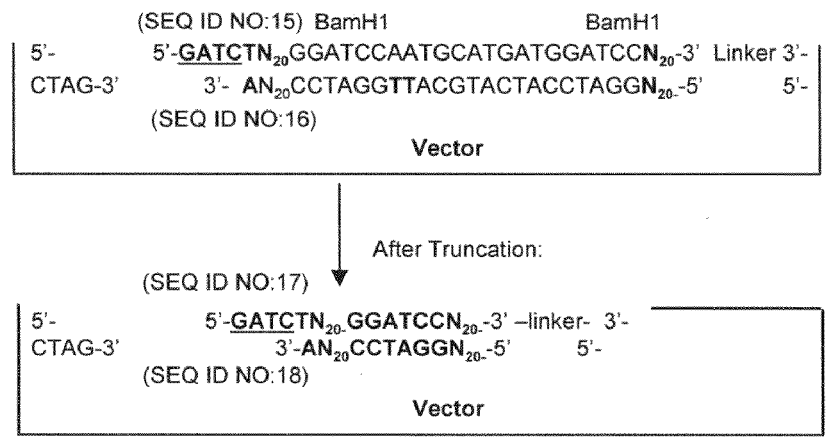

Linkers for shRNA ligation to vector

6T-EcoRV-Mlu1 linker (Y194-1 & -2, HPLC): 5'-Blunt---3'-Mlu1

```
5'-TTTTTTGATATCA----------3'      (SEQ ID NO:19)
3'-AAAAAACTATAGTGCGC-5'            (SEQ ID NO:20)
```

Gel Purification:

10 well 10% TBE NoVex Invitrogen (1.0 mm 10 well EC6225BOX $97.5)
" Xcell Surelock" Invetrogen, 1x TBS buffer
GP by "QIAEX 2 Gel Extraction kit" Cat#20021 QIAGEN

| Prep. Diffusion buffer: | Formula | Stock | 1000ul | 10 ml | 20 ml |
|---|---|---|---|---|---|
| | NH4OAc | 0.5M  7.5M | 66.7 ul | 667 ul | 1334 ul |
| | MgOAc | 10mM  1M | 10 ul | 100 ul | 200 ul |
| | EDTA(ph8) | 1mM  0.5M | 2 ul | 20 ul | 40 ul |
| | SDS | 0.1%  10% | 10 ul | 100 ul | 200 ul |
| | H2O | | 911.3 ul | 9.11 ml | 18.23 ml |
| | | | 1000 ul | 10 ml | 20 ml |

Gel + 1.5-2 Vol. Diffusion buffer
50c 1-2h (> 2h no useful)
 14K 1' spin, Transfer the supernatant (useful) into a new tube) .
- + 6 Vol. QX1
- vertex 30" QIAEX2
- +15ul QIAEX2 (10ul OK), room temp 10', vortex every 2'
- Spin 30". Remove supernatant.
- PE 500ul wash 2 times.
- Room temp. dry 15'.
- 50ul H2O X 2 , ppt ( 1.5ul G, 10 ul NaOAc, 250ul EtOH).
The yield of GP is about 30 %
- pellet in 30 ul H2O

Fig. 5 page 9

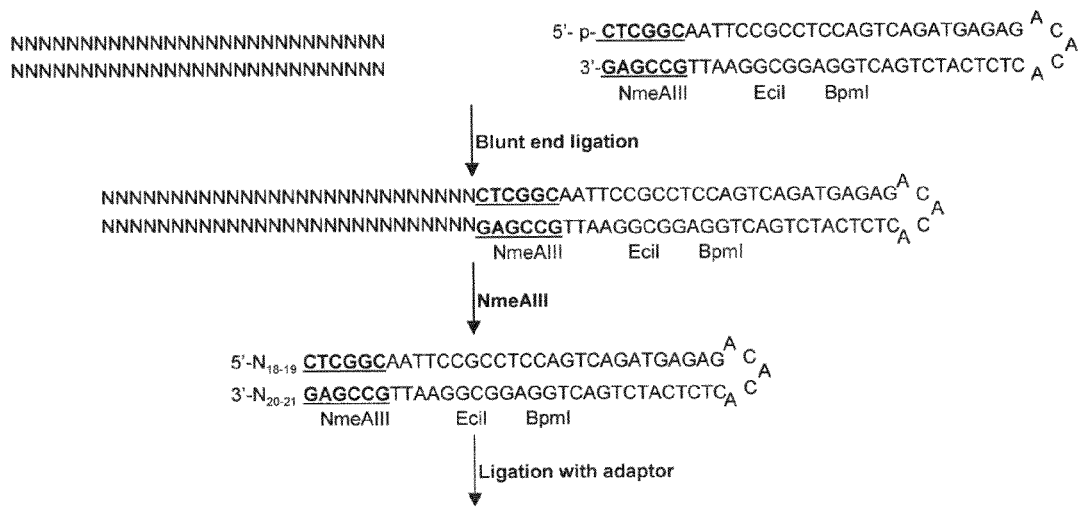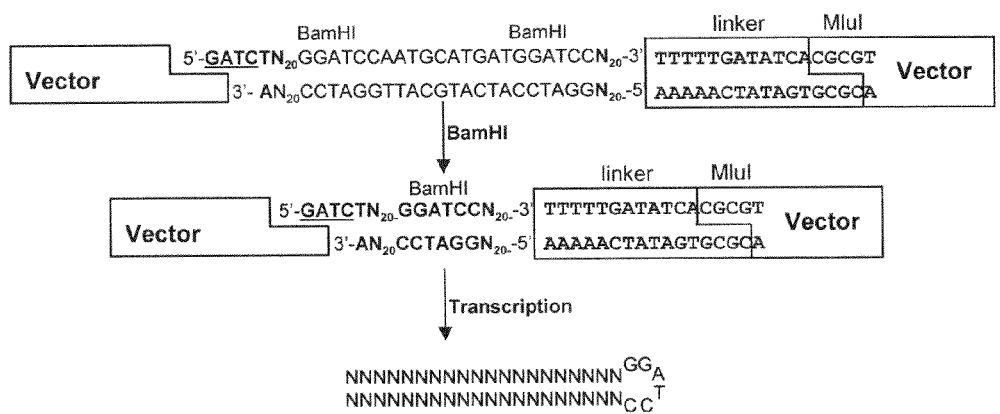
Fig. 6

SHRNA LIBRARY

BACKGROUND

RNA interference (RNAi) is a mechanism that inhibits gene expression at the stage of translation or by hindering the transcription of specific genes. RNAi targets include RNA from viruses and transposons (significant for some forms of innate immune response), and also plays a role in regulating development and genome maintenance. Small interfering RNA strands (siRNA) are key to the RNAi process, and have complementary nucleotide sequences to the targeted RNA strand. Specific RNAi pathway proteins are guided by the siRNA to the targeted messenger RNA (mRNA), where they "cleave" the target, breaking it down into smaller portions that can no longer be translated into protein. A type of RNA transcribed from the genome itself, microRNA (miRNA), works in the same way. RNAi occurs in both plants and animals, and is involved in many cellular functions, including regulating host gene expression and defense against infection by foreign organisms.

The process of RNAi begins by the presence of a double stranded RNA (dsRNA) in a cell, wherein the dsRNA contains a sense RNA having a sequence homologous to the target gene mRNA, and an antisense RNA having a sequence complementary to the sense RNA. The presence of dsRNA stimulates the activity of a ribonuclease III enzyme referred to as Dicer. Dicer is involved in the processing of the dsRNA into short pieces of dsRNA known as short inhibitory RNAs (siRNAs). Short inhibitory RNAs produced by Dicer are typically about 21 to about 23 nucleotides in length and contain about 19 base pair duplexes. siRNAs in turn stimulate an RNA-induced silencing complex (RISC) by incorporating one strand of siRNA into the RISC and directing the degradation of the homologous mRNA target.

Several methods have been used to deliver siRNAs to cells and suppress exogenous as well as endogenous gene expression. These methods include delivering synthetic siRNA molecules into cells, and vector-based methods in which siRNA is transcribed in a target cell by the vector. Certain vector-based siRNA delivery systems can result in persistent and effective suppression of gene expression, and, in certain cases expression of the siRNA can be used to select or kill cells containing the siRNA vector. Highly effective systems for delivering siRNA to a cell are established. In many vector-based methods, the siRNA is generated by the production of short hairpin RNA (shRNA), which contains a 19- to 29-bp RNA stem and a loop. In such a system, an RNA polymerase III promoter, such as H1 promoter and U6 promoter is used to drive transcription of shRNA. The shRNA is processed in the cell into siRNA through the action of the Dicer family of enzymes. Thus, the transcribed products mimic the synthetic siRNA duplexes and are as effective as the synthetic siRNA for suppressing their corresponding genes.

Certain embodiments described herein relate to a nucleic acid library for the production of shRNA in a mammalian cell.

SUMMARY

Certain aspects of this disclosure relate to a library of nucleic acid vectors, as well as a method for making the same. In certain embodiments, the library of nucleic acid vectors comprises: a plurality of nucleic acid molecules of the following formula: $S_1$—R—$S_2$ wherein, in each nucleic acid of the plurality: $S_1$ and $S_2$ are each at least 15 nucleotides in length; $S_1$ and $S_2$ are complementary to each other along their entire length; either $S_1$ or $S_2$ is complementary along its entire length to a sequence in eukaryotic mRNA; and R is the nucleotide sequence of a six base recognition site for a restriction endonuclease; and wherein $S_1$ and $S_2$ vary in nucleotide sequence between different members of the plurality. A method for amplifying a circular nucleic acid is also provided.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 6 schematically illustrates certain steps of one embodiment of the method shown in FIG. 2. From top to bottom, SEQ ID NOS:1, 7 and 29-32.

DEFINITIONS

Figure 1:
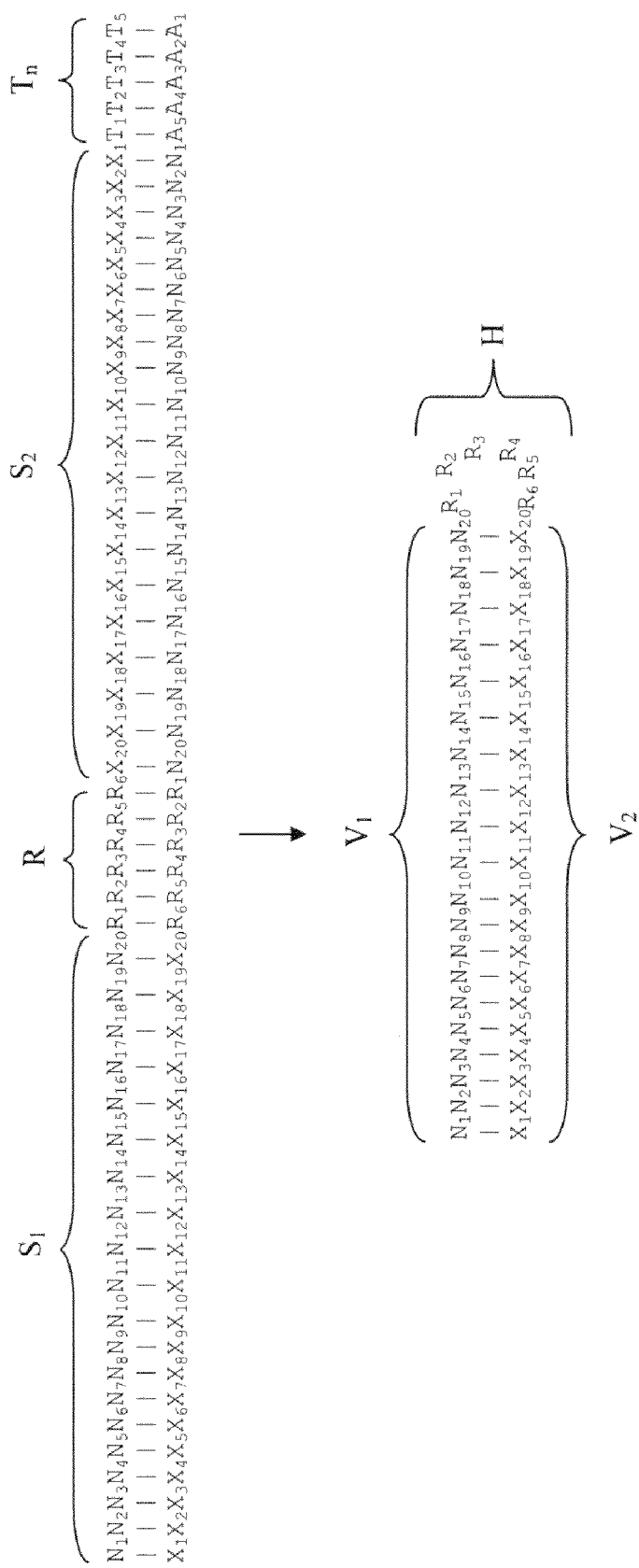
FIG. 1 schematically illustrates an exemplary nucleic acid of the formula: $S_1$—R—$S_2$, where $S_1$ and $S_2$ are each at least 20 nucleotides in length; $S_1$ and $S_2$ are complementary to each other along their entire length; either $S_1$ or $S_2$ is complementary along its entire length to a sequence in mammalian mRNA; and R is a six base recognition site for a restriction endonuclease. $T_n$ is an optional transcriptional terminator. An exemplary shRNA product encoded by the nucleic acid is illustrated at the bottom of FIG. 1.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "heterologous" refers to elements that are not normally associated with each other. For example, if a host cell produces a heterologous protein, that protein is not normally produced in that host cell. Likewise, a promoter that is operably linked to a heterologous coding sequence is a promoter that is operably linked to a coding sequence that it is not usually operably linked to in a wild-type host cell. The term "homologous", with reference to a polynucleotide or protein, refers to a polynucleotide or protein that occurs naturally in a host cell.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

A "vector" refers to a polynucleotide designed to introduce nucleic acids into one or more host cells. A vector can autonomously replicate in different host cells or can integrate into a host cell genome. In certain cases, a vector may be an adenoviral vector or other viral vector that does not replicate or integrate in the host cell. Exemplary vectors include: cloning vectors, expression vectors, shuttle vectors, plasmids, phage particles, cassettes, retroviral vectors and the like. Certain vectors may be transfected into a cell and provide for transient expression of the encoded product. Such transient expression systems are well known in the art.

An "expression cassette" as used herein means a DNA or RNA construct comprising a coding region that is operably linked to a suitable control sequence that is capable of effecting transcription and/or translation the protein in a suitable host cell. Such control sequences may include a promoter to effect transcription, an optional operator sequence to control transcription, and, optionally, enhancers and other sequences which control termination of transcription and translation. Such cassettes can be constructed in a vector in order to transfer the expression cassette into a host cell.

A "promoter" is a regulatory sequence that initiates transcription of a downstream nucleic acid.

The term "operably linked" refers to an arrangement of elements that allows them to be functionally related. For example, a promoter is operably linked to a coding sequence if it controls the transcription of the sequence.

The term "selective marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell. A light emitting protein, e.g., a fluorescent protein, is a type of selective marker.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "hybridization" refers to the process by which a strand of nucleic acid joins with a complementary strand through base pairing as known in the art. A nucleic acid is considered to be "Selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

A "coding sequence" is a DNA segment that encodes a polypeptide or shRNA.

A polypeptide or polynucleotide that is "native to the host cell" has an amino acid or nucleotide sequence that is the same as that of a polypeptide or polynucleotide that is present in an unaltered host cell. In certain instances, a cell may contain a recombinant nucleic acid containing a polynucleotide (e.g., a coding sequence) that is native to the cell. In these instances, the cell contains a recombinant nucleic acid comprising a polynucleotide having a nucleotide sequence that is also present in an unaltered version of the host cell (i.e., a host cell that does not contain any gene knockouts), at a different locus. In certain instances, a cell may contain a recombinant nucleic acid encoding a polypeptide that is native to the cell. In these instances, the cell contains a recombinant nucleic acid encoding a polypeptide having an amino acid sequence that is the same as that of a polypeptide found in an unaltered version of the host cell (i.e., a host cell that does not contain any gene knockouts). The term "endogenous" is synonymous with the term "native".

A "native promoter", with reference to a coding sequence that is operably linked to its native promoter, refers to a promoter of a wild type host cell that is operably linked to the coding sequence in that cell.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", each base of one of the nucleic acids base pairs with corresponding nucleotides in the other nucleic acid. The term "complementary" and "perfectly complementary" are used synonymously herein.

A "six base pair recognition site" is a sequence of nucleotides, which, in double stranded form, is a recognition site for a type II restriction endonuclease. To illustrate by example, GGATCC, AAGCTT and GAATTC are exemplary six base pair recognition sites for BamHI, HindIII and EcoRI, respectively, which are type II restriction endonucleases.

A "poly-dT tract" is a homopolymeric tract of thymine residues. TTTTT and TTTTTT are examples of poly-dT tracts.

If a nucleic acid "varies in nucleotide sequence" between different members of a population of nucleic acids, the sequence of nucleotides of that nucleic acid is different in each member of that population.

A "eukaryotic mRNA" is a population of mRNA molecules obtained from a eukaryotic cell. Eukaryotic mRNA can have a complexity of at least 10,000, i.e., has at least 10,000, e.g., at least 100,000 or at least $10^6$ different mRNA molecules.

A "GC dinucleotide" is a guanine immediately followed by a cytosine in a nucleotide sequence.

A "dinucleotide other than a GC dinucleotide" includes any one or more of the following: GG, GA, GT, AA, AT, AG, AC, TA, TG, TC, TT, CA, CT, CG and CC.

An "RNA polymerase III promoter" is a promoter that is recognized by an RNA polymerase III. RNA polymerase III initiates transcription of a polynucleotide downstream of an RNA polymerase III promoter.

If two sequence elements are "immediately adjacent", there are no additional nucleotides between those elements.

If a nucleic acid "provides for the production of" a product in a cell, that product is produced by a cell containing that nucleic acid. A nucleic acid that provides for the production of a product in a cell contains at least a promoter to drive the transcription of a downstream sequence to produce a product, e.g., an RNA product.

With respect to a population of nucleic acids, the term "complexity" describes the total number of different species within that population. A low complexity nucleic acid sample may contain as few as 10 different nucleic acids having different nucleotide sequences. High complexity nucleic acid sample may contain as many as $10^9$ different nucleic acids having different nucleotide sequences.

The term "phenotype altered by a nucleic acid" is intended to indicate a phenotype that would be different in the absence of the nucleic acid. For example, if cell morphology is altered by introduction of a nucleic acid into the cell, then cell morphology is a phenotype altered by the nucleic acid.

A "phenotype-stimulating agent" is a composition (e.g., hormone, drug or other bioactive agent) or environmental stimulus (e.g., light or heat) that induces a phenotype in a cell.

A "blunt end restriction enzyme" is a restriction enzyme that cleaves to produce blunt ends. SmaI, AluI and EcoRV are examples of blunt end restriction enzymes.

A "type IIs restriction enzyme recognition site" the recognition site for a type IIs restriction enzyme. Type IIs restriction enzymes cleave 10-40 bases downstream from the recognition site. Restriction enzymes can produce blunt ends, or sticky ends that have a an overhang.

A "hairpin adaptor" is an adaptor that has a stem-loop stricture, i.e., an adaptor that has a double stranded stem region and a loop region.

The term "ligating" is intended to indicate the joining of a 3' hydroxyl group of one nucleic acid to the 5' phosphate group of a another nucleic acid using a ligase.

The term "amplifying" is intended to indicate a process by which a nucleic acid is copied enzymatically using a polymerase. Amplifying can be linear or exponential.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

The term "rapidly cooling" refers to a process by which a denatured nucleic acid is rapidly transferred from a relatively high temperature (i.e., at least 90° C.) to a relatively low temperature (i.e., less then 4° C. e.g., placed "on ice") in order to preserve the nucleic acid in a denatured state.

Other definitions of terms may appear throughout the specification.

DETAILED DESCRIPTION OF EXEMPLARY EMBODIMENTS

As noted above, certain aspects of this disclosure relate to a library of nucleic acid vectors, as well as a method for making the same. In certain embodiments, the library of nucleic acid vectors comprises: a plurality of nucleic acid molecules of the following formula: $S_1$—R—$S_2$ wherein, in each nucleic acid of the plurality: $S_1$ and $S_2$ are each at least 15 nucleotides in length; $S_1$ and $S_2$ are complementary to each other along their entire length; either $S_1$ or $S_2$ is complementary along its entire length to a sequence in eukaryotic mRNA; and R is a six base recognition site for a restriction endonuclease; and wherein $S_1$ and $S_2$ vary in nucleotide sequence between different members of the plurality. A method for amplifying a circular nucleic acid is also provided.

These embodiments are described in greater detail below.

Nucleic Acid Vectors

A library of nucleic acid vectors is provided. Several general features of a nucleic acid vector of the library are illustrated in FIG. 1. With reference to FIG. 1, a nucleic acid vector of the library contains the following regions: $S_1$, R and $S_2$. As illustrated in FIG. 1, $S_1$ and $S_2$ are each at least 15 nucleotides in length (e.g., 15, 16, 17, 18, 19, 20, 21, 22, 23, 24, 25, 26 27 or 28 nucleotides in length, up to about 35 or 40 or more nucleotides in length, depending on the method by which the library is made) and complementary to each other along their entire lengths. R is a six base palindromic recognition site for a restriction endonuclease, many of which are known and need not be described in detail. As illustrated, there are no intervening bases between $S_1$, R and $S_2$. Depending on the orientation of the insertion of a fragment cloned early in the production of the library, either $S_1$ or $S_2$ is complementary along its entire length to a sequence in eukaryotic mRNA, e.g., mammalian mRNA. As such, the contiguous sequence of nucleotides of $S_1$ is either perfectly complementary to or perfectly identical to (after T residues are substituted for U residues) a nucleotide sequence in eukaryotic mRNA. The nucleotide sequences of $S_1$ and $S_2$ vary in nucleotide sequence between the various members of the library. In other words, the nucleotide sequence of $S_1$ differs between the different members of the library and $S_2$, having a nucleotide sequence that is complementary to $S_1$, also differs between the different members of the library.

The nucleic acid vectors of the library encode a short hairpin RNA of the formula $V_1$—H—$V_2$, as shown in FIG. 1, where the nucleotide sequences of $V_1$, $V_2$ and H are determined by the nucleotide sequences of the $S_1$, $S_2$ and R, as described above. As shown in FIG. 1, the $V_1$ and $V_2$ regions base-pair with each other to form the "stem" of the hairpin, and H forms the "loop" of the hairpin.

In certain embodiments and as shown in FIG. 1, the nucleic acids of the library may be of the formula: $S_1$—R—$S_2$-$T_n$, where $S_1$, R and $S_2$ are described above, and $T_n$ is an RNA polymerase III terminator. Such terminators are known and need not be described in detail. In one embodiment, terminator $T_n$ may be a poly-dT tract of length n, where n is at least 5, e.g., at least 6, at least 7. In addition, the nucleic acids of the library may be operably linked to a promoter that is immediately 5' to the $S_1$ region. As such, in certain embodiments, the subject nucleic acids may comprise an expression cassette for the transcription of the $S_1$—R—$S_2$ region, where the expression cassette is of the formula P—$S_1$—R—$S_2$-$T_n$, where P is a promoter and $T_n$ is a terminator. The promoter may be an RNA polymerase II promoter (such as that described in Zeng RNA 2003 9:112-123) or an RNA polymerase III. Suitable RNA polymerase III promoters are known (see, e.g., published US patent applications 20050130184 and 20050130919, and U.S. Pat. No. 6,852,535) and include the H1, 5S, U6, adenovirus VA1, Vault, telomerase RNA, tRNA genes. A promoter that is active in mammalian cells may be used, although a non-mammalian promoter may be used if the library is to be employed in non-mammalian cells. The promoter may be constitutively active, or it may be inducible, for example.

As such, in certain cases, when introduced into a host cell (e.g., a mammalian host cell), the subject library provides for the production of hairpin RNA of the formula $V_1$—H—$V_2$, where $V_1$ and $V_2$ are complementary to each other and are each at least 15 nucleotides in length and H is the single stranded nucleotide sequence of a six base recognition site for a restriction endonuclease.

In certain embodiments, the library may contain member nucleic acids in which the dinucleotide at the 3' end of the $S_1$ region (nucleotides $N_{19}$ and $N_{20}$ as shown in FIG. 1) is not a GC dinucleotide. In certain of these embodiments, all of the members of the library may have an $S_1$ region 3' dinucleotide that is not a GC dinucleotide. In other of these embodiments, the library may contain: a) members in which the $S_1$ region has a GC dinucleotide at their 3' end; and b) members in which the $S_1$ region has a dinucleotide other than a GC dinucleotide at their 3' end. The identities of the dinucleotide at the 3' end of the $S_1$ region depends on the restriction enzymes in the first step of library construction. In certain embodiments, the subject library may contain any 1, 2, 3, 4, 5, 6, 7, 8, 9, or 10 or more of the following dinucleotides: GG, GA, GT, AA, AT, AG, AC, TA, TG, TC, TT, CA, CT, CG, CC and, optionally, GC, at the 3' end of the $S_1$ region, depending on the enzymes restriction enzyme used for digestion.

In certain embodiments, the complexity of the library, i.e., the total number of different species within the nucleic acid population, is at least 10, at least 100, at least 1,000, at least 10,000, at least 100,000, at least $10^6$, at least $10^7$ or greater, up to $10^9$ or more in certain cases.

In a particular embodiment the vector may be suitable for introduction and maintenance in a eukaryotic host cell, e.g., a mammalian host cell, either extrachromasomally or integrated the genome of the host cell. A wide variety of such vectors are known. In one embodiment, the vector is a viral vector such as a retroviral vector, e.g., a lentiviral vector, that can stably integrate into the genome of a mammalian host cell. Retroviral vectors are well known, and include those described in 20070048285, 20070042352, 20060258006, 20060035371, 20030166251 and 20020106790, for example.

Also provided is a population of cells comprising the library of nucleic acid vectors described above. The cells may be, e.g., bacterial cells that are used in the production and storage of the nucleic acid vectors, or eukaryotic cells that are used in a screening assay described below. Because many cells in the population may contain the same nucleic acid vector, the complexity of the nucleic acid library in a population of cells may be lower than the total number of cells in the population. In certain embodiments, there may be more than 1,000, 10,000, 100,000, $10^6$, $10^7$, $10^8$, or $10^9$ or more cells in the population of cells. The cells, may be, for example, E. coli cells, nematode cells, plant cells (e.g., Arabidopsis or corn cells) or animal cells (e.g., bird, fish, reptile, mammalian or insect cells). In particular embodiments, the cells may be mammalian, e.g., human, mouse, rat or monkey cells. In certain embodiments the host cell may have an intact RNA pathway which includes dicer and RNA-induced silencing complexes.

Method for Making a Library of Nucleic Acid Vectors

Also provided herein is a method of producing a library of nucleic acid vectors. This method is described with reference to FIG. 2.

Figure 2:
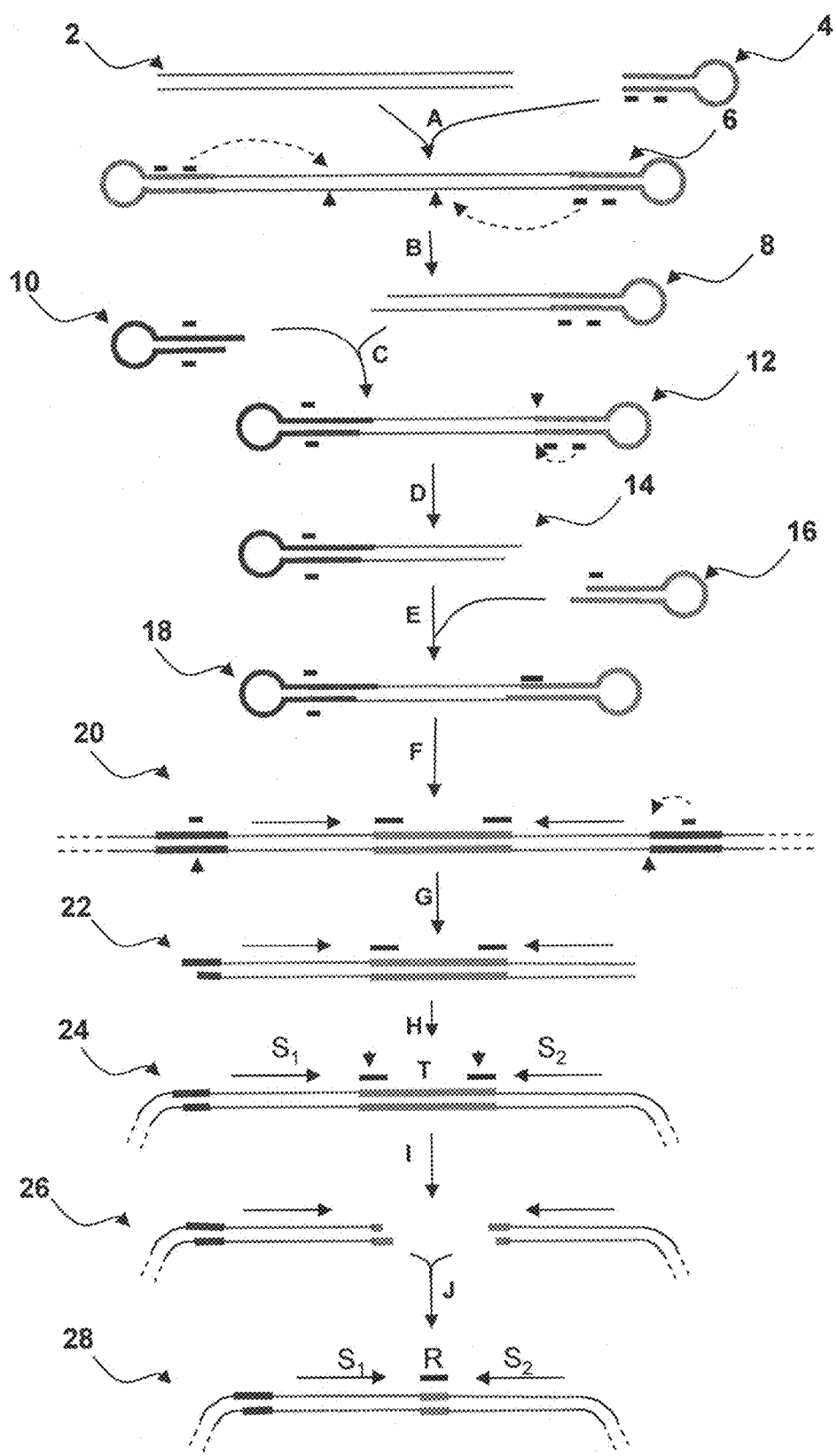
FIG. 2 schematically illustrates one embodiment of a method by which the nucleic acid shown in FIG. 1 may be made.

The first ligation step A comprises: b) ligating a first double stranded adaptor 4 comprising a first and a second type IIs restriction enzyme recognition site to blunt end fragments 2 to produce first adaptor-ligated fragments 6. The blunt end fragments may be blunt at either or both ends. In certain embodiments and as shown in FIG. 2, the blunt end fragments may be blunt at both ends. The blunt end fragments may be produced by any of a number of different methods, e.g., using a restriction enzyme or by other cleavage method followed by a polishing step that produces blunt ends. In certain embodiments, the blunt end fragments may be produced by digesting a sample containing target double stranded nucleic acid with a blunt end restriction enzyme to produce the blunt end fragments. In one embodiment, the target double stranded nucleic acid may be digested with multiple enzymes that cut at different sites (e.g., at least 5, 6, 7, 8, 9 or 10 or more different enzymes). The digestion may be done in a single tube, or in separate tubes that are later combined. In this step, the first double stranded adaptor 4 may be a hairpin adaptor. In certain cases, the sample may contain double stranded cDNA (e.g., cDNA made from mRNA obtained from eukaryotic cells, such as subtracted cDNA), however, other double stranded material, e.g., genomic DNA or sequences of random nucleotide sequence, may also be used.

The first digestion step B comprises: digesting the adaptor-ligated fragments 8 with the first type IIs restriction enzyme to produce digested fragments 8 that contain the first double stranded adaptor and the second type IIs restriction enzyme recognition site. As indicated by the dotted arrow line, the first type IIs restriction enzyme cleaves in a sequence of the target double stranded nucleic acid. In certain embodiments, the first type IIs restriction enzyme may be one that cuts at least 15 bases pairs away from its recognition site (e.g., 10 to about 40 bp away, e.g., about 15 to about 30 bp, e.g., 18 bp, 19 bp, 20 bp, 21 bp, 22 bp, 23 bp, away, etc.). Exemplary enzymes that can be used in this digestion step include MmeI and NmeAIII, although others could be used. NmeAIII cuts 20 to 21 bases away from its recognition site and leaves a two nucleotide overhang.

The second ligation step C comprises: ligating a first hairpin adaptor 10 that contains restriction enzyme recognition sites to the digested fragments 8 to produce second adaptor-ligated fragments 12. The restrictions enzyme recognition sites, which in certain cases may be for one type IIs restriction enzyme and one type II restriction enzyme, are used later in the method. The first hairpin adaptor may contain a "NN" dinucleotide at its 3' end, where N is any nucleotide. When this adaptor is folded into a hairpin, the "NN" dinucleotide forms an overhang.

The second digestion step D comprises: e) digesting the second adaptor-ligated fragments 12 with the second type IIs restriction enzyme to produce a population of hairpin-containing digestion products 14. As shown in FIG. 2, the second type IIs restriction enzyme site is found in the first double stranded adaptor 4. In certain embodiments and as shown by the dotted line arrow in FIG. 2, the second type IIs restriction enzyme site cuts at the junction between the first double stranded adaptor 4 and the blunt end fragments 2.

The third ligation step E comprises: ligating a second hairpin adaptor 16 to the population of hairpin products 14 to produce a population of circular nucleic acid molecules 18. In certain embodiments, the second hairpin adaptor may contain an "NN" dinucleotide at its 3' end, where N is any nucleotide. When this adaptor is folded into a hairpin, the "NN" dinucleotide forms an overhang. In certain embodiments, this adaptor may contain a first type II restriction enzyme site immediately adjacent to the "NN" dinucleotide overhang.

After the population of circular nucleic acid molecules 18 is made, the population of circular nucleic acid molecules may be amplified via step F using rolling circle amplification to produce a population of linear double stranded nucleic acids 20. While a number of one-step or two step rolling circle-based amplification methods may be employed in this step (see, e.g., published U.S. patent application US20080021205), one embodiment may be done using the following method: a) combining i. the population of circular nucleic acid molecules, ii. a primer that anneals to the population of circular nucleic acid molecules and iii. a Ø29 polymerase under polymerization conditions (i.e., conditions under which the polymerase is active) to produce a single-stranded template; b) denaturing the single stranded template to make a denatured template, e.g., by heating the single stranded template to a temperature in the range of 90° C.-100° C. for at least 1 minute; c) rapidly cooling the denatured template (e.g., by placing the denatured template at below 5° C., such as on ice or in liquid nitrogen, for at least 1 minute); and d) combining i. the denatured template, ii. a primer that anneals to the denatured template and iii. a proofreading DNA polymerase under polymerization conditions to produce the population of linear nucleic acids. The proofreading DNA polymerase may be, for example, a bacterial, e.g., *E. coli*, DNA polymerase I or any catalytically active fragment or variant thereof, e.g., a Klenow fragment.

Figure 3:
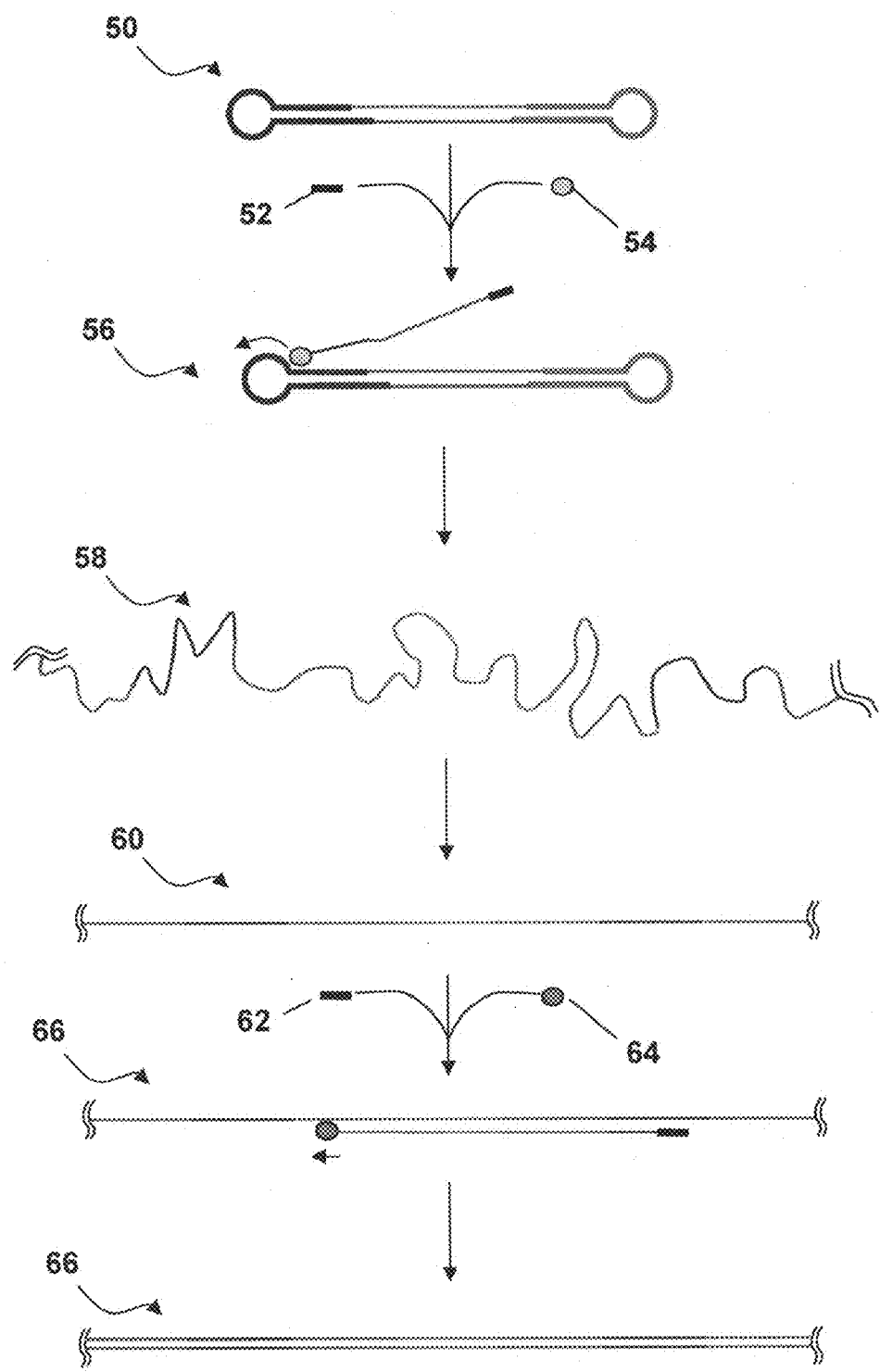
FIG. 3 schematically illustrates one embodiment of a method for amplifying a circular nucleic acid.

The above-described amplification method may be employed to amplify any short, circular DNA molecule, including those that are "bar-bell" shaped, i.e., those that have two single stranded loop regions and a double stranded stem region such as nucleic acid 18 in FIG. 2, or those that are double stranded for their entire length. As such, an amplification method is also provided. With reference to FIG. 3, this amplification method comprises: a) combining a circular DNA molecule 50, a primer that anneals to the circular DNA molecule 52 and a Ø29 polymerase 54 under polymerization conditions to initiate primer extension 56 and produce a single-stranded template 58; b) denaturing the single-stranded template to make a denatured template 60; c) rapidly cooling the denatured template (not shown in FIG. 2); and combining the denatured template 60, a primer that anneals to the denatured template 62 and a proofreading DNA polymerase 64 under polymerization conditions to initiate primer extension 66 and produce a double stranded amplification product 66. In certain embodiment, the initial circular DNA molecule may be less than 1,000 nucleotides, e.g., less than 500 nucleotides, less than 200 nucleotides, less than 100 or less than 80 nucleotides, in length. In one embodiment, circular DNA may be 90-120 bases in length.

The third digestion step G comprises digesting the population of linear double stranded nucleic acids 20 with restriction enzymes that recognize the restriction enzyme recognition sites (as indicated by the short vertical arrows) of the first hairpin adaptor 10 to produce a population of clonable fragments 22. The clonable fragments comprising nucleic acids of the formula: $S_1$-T-$S_2$, where: $S_1$ and $S_2$ are complementary to each other and are each at least 15 nucleotides in length and T is an amplification product of the second hairpin adaptor and comprises two six base recognition sites for a second restriction endonuclease, e.g., a type II restriction endonuclease. As noted above, this digestion step may be done using any pair of restriction enzymes. However, in certain embodiments and as indicated by the dotted line arrow in FIG. 2, the digestion may done using: a) a type IIs restriction enzyme that cleaves at the junction between the first hairpin adaptor primer 10 and the target double stranded nucleic acid 2 to produce blunt ends and b) a different enzyme, e.g., a type II restriction enzyme, that cleaves within the second first hairpin adaptor primer 10. In this embodiment, clonable fragments 22 have one blunt end and one "sticky" end, i.e., an end with an overhang, that can be readily cloned into a vector that is appropriately digested, can be produced.

The fourth ligation step H comprises ligating the clonable fragments 22 into a compatibly digested vector to produce a population of circular vectors 24. In certain embodiments, the clonable fragments may be ligated directly into the vector. In other embodiments, the clonable fragments may be ligated via a linker, as shown in the experimental section of this disclosure. In certain embodiments, the resultant vectors 24 may have a promoter and terminator flanking the insert to provide an expression cassette for the production of hairpin RNA. This ligation step may optionally include bulking up the circular vectors by transforming cells with the population of circular vectors and re-isolating the population of circular vectors from said cells prior to step the next step.

The fourth digestion step I comprises digesting the population of circular vectors 24 with the second restriction enzyme to produce digested vectors 26 (see vertical arrows in FIG. 2). The ends of the digested vectors are cohesive in that they can be re-ligated.

Finally, the digested vectors are intramolecularly ligated in step J to produce a library of nucleic acids vectors 28 comprising a plurality of nucleic acid molecules of the formula: $S_1$—R—$S_2$, wherein $S_1$ and $S_2$ are as set forth above, and R is the nucleotide sequence of a six base recognition site for the second restriction endonuclease.

At this point, the library of nucleic acid vectors may be stored, either as DNA dissolved in a buffer, or in cells. The library may be used in a screening assay described in greater detail below.

Certain embodiments of the above-described method provide for the production of a plurality of nucleic acid molecules of the following formula: $S_1$—R—$S_2$ wherein, in each nucleic acid of said plurality: $S_1$ and $S_2$ are each at least 15 nucleotides in length; $S_1$ and $S_2$ are complementary to each other along their entire length; either $S_1$ or $S_2$ is complementary along its entire length to a sequence in mammalian mRNA; and R is a six base recognition site for a restriction endonuclease; and wherein $S_1$ and $S_2$ vary in nucleotide sequence between different members of the plurality, as described above.

Methods of Use

Also provided is a method of screening that uses the above-described library of nucleic acids. The subject library may be employed in drug discovery methods for identifying bioactive shRNAs, for example.

The general concepts of similar screening methods are generally described in a variety of publications, e.g., U.S. Pat. Nos. 6,153,380, 6,455,247, 6,897,031 and 6,461,813, and US published patent application 20030190684, and, as such, need not be described in any great detail.

In general terms, this method comprises transfecting a generally homogeneous population of cells with the above-described library, and screening the population of transfected cells for a cell having a phenotype altered by a nucleic acid.

The method may further involve identifying a cell as having a phenotype altered by the nucleic acid. In certain embodiments, the screening may be done by fluorescence activated cell sorting (FACS), although many other methods of screening (e.g., colony-based assays in which colonies of cells are grown and screened for a phenotype) may be employed. In certain cases, the method may further include isolating the cell having an phenotype altered by the nucleic acid and, optionally, determining the sequence of the $S_1$ region (which, can be determined by sequencing the $S_2$ region) of the nucleic acid introduced into that cell. The identified sequence can then be used as, or used to design, therapeutic agents, for example, or as a research tool for producing a phenotype.

In certain embodiments, the phenotype of the cells may be a cancer-related phenotype (e.g., a cell division or cell cycle, apoptosis or metastasis phenotype), an inflammatory phenotype (e.g., a degranulation or activation phenotype), a symmetric or asymmetric cell division, an infectious disease-related phenotype (e.g., a phenotype induced by infection of an infectious disease), or a phenotype induced by a phenotype-inducing stimulus (e.g., a phenotype induced by exposure to a chemical or environmental agent), for example. In certain cases, the phenotype may be a gene expression phenotype in which a reporter gene is detected. Other embodiments may involve cell staining with antibodies or other detectable agents and the like.

EXPERIMENTAL

The following examples are provided in order to demonstrate and further illustrate certain preferred embodiments and aspects of the present invention and are not to be construed as limiting the scope thereof.

EXAMPLE 1

Library Construction—Summary

Figure 4:
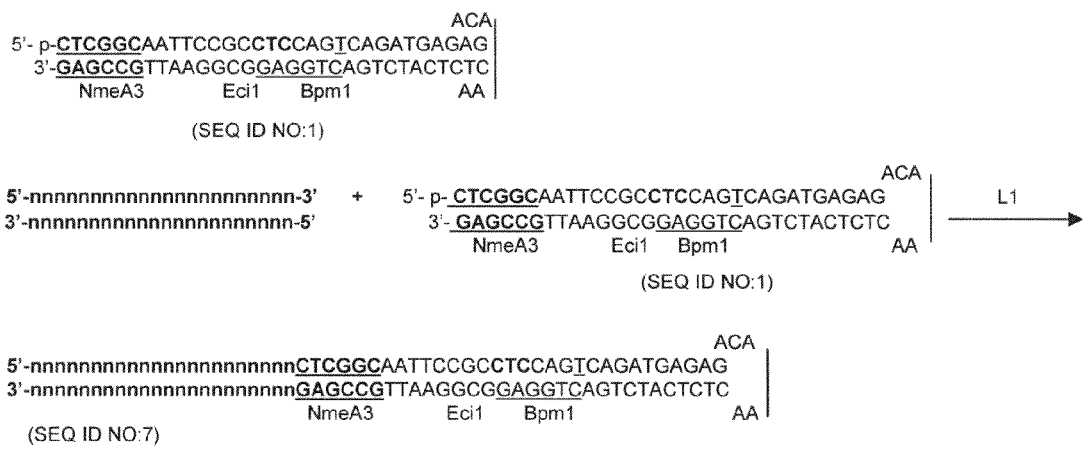
FIG. 4 sets forth the nucleotide sequences and structures of several adaptors and primers used herein. Adaptor1: SEQ ID NO:1; Adaptor 2: SEQ ID NO:2; Adaptor 3: SEQ ID NO:3; ext-R13-8R primer: SEQ ID NO:4; ext-R13-10F primer: SEQ ID NO:5.

The sequences of the adaptors and primers used in certain steps of this method are shown in FIG. 4.

Step 1: A double strand cDNA or a cDNA library is digested by a mixture of five restriction enzymes Alu1, BstU1, Hae3, Rsa1 and HpyCH4V to result in blunt ended fragments of 50-200 bp in length.

Step 2: The fragmented cDNA is ligated to a hairpin-shaped synthetic oligonucleotide adaptor1 which containing the recognition sequence of NmeAIII, Bmp1 and Eci1. The restriction enzyme NmeAIII can cleaves 20-21 bp away from its recognition sequence and leaves a two-nucleotide overhang.

Step 3: Ligate a hairpin-shaped synthetic oligonucleotide adaptor3 to the NmeAIII-digested ds-cDNA from step2. Adaptor 3 contains three specific restriction sites (Bbs1,Bgl 11 and Mly1) for cloning into retroviral expression vector. Adaptor 1 and adaptor 3 ligated DNA fragments are then purified by 10% Novex TBE gel and get a 75 bp DNA.

Step 4: Digestion the DNA from step 3 by Bpm1 and Eci1.

Step 5: The fragmented DNA from step 4 are ligated to a hairpin-shaped synthetic oligo adaptor 2 which include BamH1 and form a hairpin loop with sense and anti-sense strands with complementary NN overhang.

Step 6: The DNAs from step 5 are digested by Bpm1, then purified by 10% Novex TBE gel and get a 52 bp DNA fragments.

Step 7: Amplify the DNAs by phi29 polymerase using primers ext-R13-8R to create linear single stranded DNAs at 30° C. for 12-16 hours, then heat at 67° C. for 12 minutes to inactivate the phi29 polymerase.

Step 8: After heating at 94° C. for 3 mins and cooled in dry ice immediately for 3 mins, the linear single stranded DNAs are then made into double stranded DNA encoding shRNA molecules using DNA polymerase1 using primer ext-R13-10F.

Step 9: The amplified double stranded DNA is then digested by Bbs1, Bgl 11, and Mly1. Then DNA is purified by 10% Novex TBE gel and get a 67 bp shRNAs with 5'-GATC overhang and 3'-blunted cloning sites.

Step 10: Ligate the shRNA from step 9 and the 6T-EcoRV-MluI linker into BamHI, MluI digested EFS-U3U6TO-TRAdsrGFP retroviral expression vector or LRUkfc lentiviral vector.

Step 11: Transform DNA into Top10 electro-competent cells, then isolate plasmid DNA for shRNA library.

Step 12: Truncation of shRNA library DNA by BamH1 and purify the DNA by 0.8% agarose gel.

Step 13: The DNA from step 12 is re-ligated itself and retransform into Electro-Top10 competent cells.

Step 14: Isolate the plasmid DNA. The shRNA libraries including 5-20 million primary clones and more than 90% correct sequence and 6 bp hairpin loop.

Figure 5:
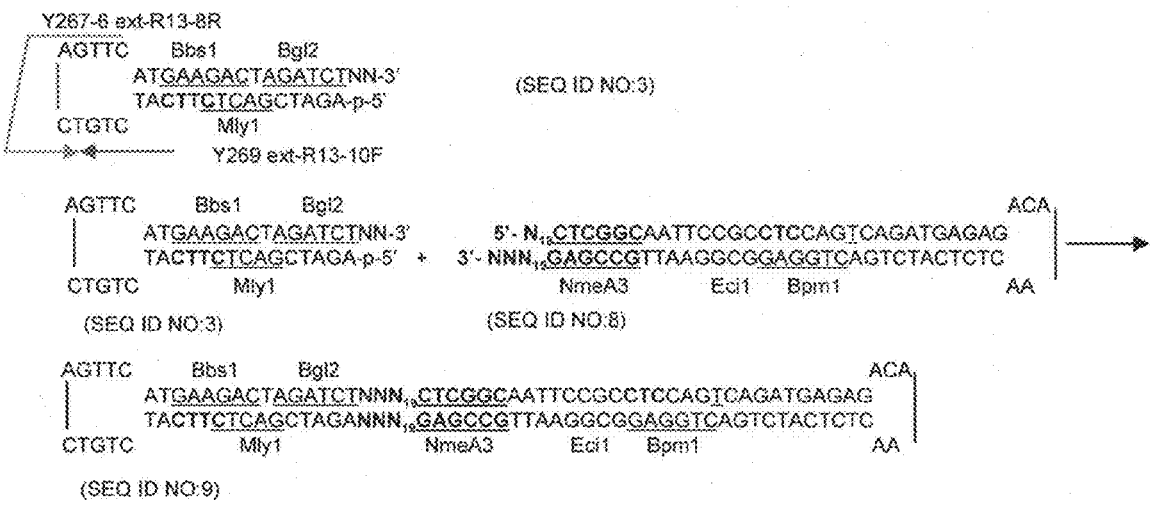
FIG. 5 sets forth in detail an embodiment of a method by which a nucleic acid library can be made.

This method is set forth in greater detail in FIG. 5

FIG. 6 illustrate steps 2, 3, 11 and 12, as well as the resultant shRNA encoded by the final product.

The method described above provides an shRNA region (at least 20-21 bp), each nucleotide of which is complementary to its target mRNA, which is 1-2 bp more than Mme1-based shRNA methods, which only clone fragments containing a GC end. The amplification strategy used provides a large amount and high quality, nonmutated shRNA for library construction. Also, the hairpin region of the shRNA produced contains only 6 bases, so the functional activity can be much improved.

EXAMPLE 2

Screening Assay

Axl, a receptor tyrosine kinase with a structure novel among tyrosine kinases, is a key regulator of tumor angiogenesis. shRNAs that down-regulate expression of AXL were identified.

An AXL shRNA library was created from the 2.9 kb AXL cDNA using the method described above. The shRNA library retroviral vector has a GFP expression cassette for selection. The amphotropic retroviral packaging cell line, phoenix A, is used for virus production.

$3 \times 10^6$ Hela cells were infected with the viruses encoding the AXL shRNA library. The infected cells were incubated at 37° C. in 5% CO2 for 5 days. $2 \times 10^7$ cells were harvested and GFP positive/anti-AXL Ab staining negative cells (10% of total population) were sorted. The GFP positive/AXL negative cells were expanded for a week and sorted again.

After sorting, single cell clones of GFP positive/AXL negative cells were established. 69 GFP positive clones were picked and analyzed for inhibition of AXL expression. 28 clones showed more than 90% reduction of AXL expression, whereas others showed 50% to 90% reduction.

23 shRNA inserts from the 28 clones were amplified by PCR and sequenced. The 23 inserts represented 6 different shRNAs.

The shRNAs were ligated into the retroviral vectors. The virus encoding each shRNA was infected to naïve Hela cells. AXL expression in GFP positive and negative population was analyzed. Three shRNAs showed more than 8 fold reduction of AXL expression.

The invention claimed is:

1. A method of producing a library of nucleic acids, comprising:

a) ligating a first double stranded adaptor comprising a first and a second type IIs restriction enzyme recognition sites to blunt end fragments to produce first adaptor-ligated fragments;

b) digesting said adaptor-ligated fragments with said first type IIs restriction enzyme to produce digested fragments comprising said first double stranded adaptor and said second type IIs restriction enzyme recognition site;

c) ligating a first hairpin adaptor comprising restriction enzyme recognition sites to said digested fragments to produce second adaptor-ligated fragments;

d) digesting said second adaptor-ligated fragments with said second type IIs restriction enzyme to produce a population of hairpin-containing digestion products;

e) ligating a second hairpin adaptor to said population of hairpin products to produce a population of circular nucleic acid molecules;

f) amplifying said population of circular nucleic acid molecules using rolling circle amplification to produce a population of linear double stranded nucleic acids;

g) digesting said population of linear double stranded nucleic acids with restriction enzymes that recognizes said restriction enzyme recognition sites of said first hairpin adaptor to produce a population of clonable fragments comprising nucleic acids of the formula:

$S_1$-T-$S_2$, wherein: $S_1$ and $S_2$ are complementary to each other and are each at least 15 nucleotides in length and T is an amplification product of said second hairpin adaptor and comprises two six base recognition sites for a second restriction endonuclease;

h) ligating said clonable fragments into a vector to produce a population of circular vectors;

i) digesting said population of circular vectors with said second restriction enzyme to produce digested vectors; and j) intramolecularly religating said digested vectors to produce said library of nucleic acids vectors comprising a plurality of nucleic acid molecules of the formula:

$S_1$—R—$S_2$, wherein S1 and S2 are as set forth above, and R is a six base recognition site for said second restriction endonuclease.

2. The method of claim 1, wherein said target double stranded nucleic acid is double stranded cDNA made from mRNA isolated from a mammalian cell.

3. The method of claim 1, wherein said method comprises, before said ligating step: digesting said sample comprising target double stranded DNA with a plurality of different blunt end restriction enzymes that cleave at different sites to produce said blunt end fragments.

4. The method of claim 1, wherein said first double stranded adaptor is a hairpin adaptor.

5. The method of claim 1, wherein digesting step g) is done by digesting said population of linear double stranded nucleic acids with a type II restriction enzyme and a type IIs restriction enzyme that cleave at sites present within said second hairpin.

6. The method of claim 1, wherein said amplifying step f) is done by:

combining said population of circular nucleic acid molecules, a primer that anneals to said population of circular nucleic acid molecules and a Ø29 polymerase under polymerization conditions to produce a single-stranded template;

denaturing said single stranded template to make a denatured template;

rapidly cooling said denatured template; and combining said denatured template, a primer that anneals to said denatured template and a proofreading DNA polymerase under polymerization conditions to produce said population of linear nucleic acids.

7. The method of claim 6, wherein said method comprises transforming cells with said population of circular vectors of step h), and re-isolating said population of circular vectors from said cells prior to step i).

* * * * *

SEQUENCE LISTING

<160> NUMBER OF SEQ ID NOS: 32

<210> SEQ ID NO 1
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 1
ctcggcaatt ccgcctccag tcagatgaga gacacactct catctgactg gaggcggaat    60
tgccgag                                                              67

<210> SEQ ID NO 2
<211> LENGTH: 24
<212> TYPE: DNA
<213> ORGANISM: Artificial Sequence
<220> FEATURE:
<221> NAME/KEY: misc_feature
<222> LOCATION: 23, 24
<223> OTHER INFORMATION: n = A,T,C or G
<220> FEATURE:
<223> OTHER INFORMATION: Synthetic oligonucleotide

<400> SEQUENCE: 2
ggatccaatg catgatggat ccnn                                           24

<210> SEQ ID NO 3
<211> LENGTH: 42
<212> TYPE: DNA
<213> ORGANISM: Artificial Sequence
<220> FEATURE:
<221> NAME/KEY: misc_feature
<222> LOCATION: 41, 42
<223> OTHER INFORMATION: n = A,T,C or G
<220> FEATURE:
<223> OTHER INFORMATION: Synthetic oligonucleotide

<400> SEQUENCE: 3
agatcgactc ttcatctgtc agttcatgaa gactagatct nn                       42

<210> SEQ ID NO 4
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 4 gaactgac                                                              8

<210> SEQ ID NO 5
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 5 cttcatct                                                              8

<210> SEQ ID NO 6
<211> LENGTH: 67
<212> TYPE: DNA
<213> ORGANISM: Artificial Sequence

```
<220> FEATURE:
<223> OTHER INFORMATION: Synthetic oligonucleotide

<400> SEQUENCE: 6
ctcggcaatt ccgcctccag tcagatgaga gacaaactct catctgactg gaggcggaat    60
tgccgag                                                              67

<210> SEQ ID NO 7
<211> LENGTH: 111
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21, 22, 90, 91, 92, 93, 94, 95, 96, 97, 98,
      99, 100, 101, 102, 103, 104, 105, 106, 107, 108, 109, 110,
      111
<223> OTHER INFORMATION: n = A,T,C or G
<220> FEATURE:
<223> OTHER INFORMATION: Synthetic oligonucleotide

<400> SEQUENCE: 7
nnnnnnnnnn nnnnnnnnnn nnctcggcaa ttccgcctcc agtcagatga gagacaaact    60
ctcatctgac tggaggcgga attgccgagn nnnnnnnnnn nnnnnnnnnn n             111

<210> SEQ ID NO 8
<211> LENGTH: 107
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 87, 88, 89, 90, 91, 92, 93, 94, 95, 96, 97, 98,
      99, 100, 101, 102, 103, 104, 105, 106, 107
<223> OTHER INFORMATION: n = A,T,C or G
<220> FEATURE:
<223> OTHER INFORMATION: Synthetic oligonucleotide

<400> SEQUENCE: 8
nnnnnnnnnn nnnnnnnnnc tcggcaattc cgcctccagt cagatgagag acaaactctc    60
atctgactgg aggcggaatt gccgagnnnn nnnnnnnnnn nnnnnn                   107

<210> SEQ ID NO 9
<211> LENGTH: 149
<212> TYPE: DNA
<213> ORGANISM: Artificial Sequence
<220> FEATURE:
<221> NAME/KEY: misc_feature
<222> LOCATION: 21, 22, 23, 24, 25, 26, 27, 28, 29, 30, 31, 32, 33, 34,
      35, 36, 37, 38, 39, 40, 41, 109, 110, 111, 112, 113, 114, 115,
      116, 117, 118, 119, 120, 121, 122, 123, 124, 125, 126, 127,
      128, 129
<223> OTHER INFORMATION: n = A,T,C or G
<220> FEATURE:
<223> OTHER INFORMATION: Synthetic oligonucleotide

<400> SEQUENCE: 9
agttcatgaa gactagatct nnnnnnnnnn nnnnnnnnnn nctcggcaat tccgcctcca    60
gtcagatgag agacaaactc tcatctgact ggaggcggaa ttgccgagnn nnnnnnnnn    120 nnnnnnnnna gatcgactct tcatctgtc                                    149

<210> SEQ ID NO 10
<211> LENGTH: 80
<212> TYPE: DNA
<213> ORGANISM: Artificial Sequence
<220> FEATURE:
```

```
<221> NAME/KEY: misc_feature
<222> LOCATION: 1, 2, 3, 4, 5, 6, 7, 8, 9, 10, 11, 12, 13, 14, 15, 16,
      17, 18, 19, 60, 61, 62, 63, 64, 65, 66, 67, 68, 69, 70, 71,
      72, 73, 74, 75, 76, 77, 78, 79, 80
<223> OTHER INFORMATION: n = A,T,C or G
<220> FEATURE:
<223> OTHER INFORMATION: Synthetic oligonucleotide

<400> SEQUENCE: 10
nnnnnnnnnn nnnnnnnnna gatcgactct tcatctgtca gttcatgaag actagatctn        60
nnnnnnnnnn nnnnnnnnnn                                                    80

<210> SEQ ID NO 11
<211> LENGTH: 69
<212> TYPE: DNA
<213> ORGANISM: Artificial Sequence
<220> FEATURE:
<221> NAME/KEY: misc_feature
<222> LOCATION: 68, 69
<223> OTHER INFORMATION: n = A,T,C or G
<220> FEATURE:
<223> OTHER INFORMATION: Synthetic oligonucleotide

<400> SEQUENCE: 11
ctcggcaatt ccgcctccag tcagatgaga gacaaactct catctgactg gaggcggaat        60 tgccgagnn                                                                69

<210> SEQ ID NO 12
<211> LENGTH: 104
<212> TYPE: DNA
<213> ORGANISM: Artificial Sequence
<220> FEATURE:
<221> NAME/KEY: misc_feature
<222> LOCATION: 21, 22, 23, 24, 25, 26, 27, 28, 29, 30, 31, 32, 33, 34,
      35, 36, 37, 38, 39, 40, 41, 64, 65, 66, 67, 68, 69, 70, 71,
      72, 73, 74, 75, 76, 77, 78, 79, 80, 81, 82, 83, 84
<223> OTHER INFORMATION: n = A,T,C or G
<220> FEATURE:
<223> OTHER INFORMATION: Synthetic oligonucleotide

<400> SEQUENCE: 12
agttcatgaa gactagatct nnnnnnnnnn nnnnnnnnnn nggatccaat gcatgatgga        60
tccnnnnnnn nnnnnnnnnn nnnnagatcg actcttcatc tgtc                        104

<210> SEQ ID NO 13
<211> LENGTH: 104
<212> TYPE: DNA
<213> ORGANISM: Artificial Sequence
<220> FEATURE:
<221> NAME/KEY: misc_feature
<222> LOCATION: 21, 22, 23, 24, 25, 26, 27, 28, 29, 30, 31, 32, 33, 34,
      35, 36, 37, 38, 39, 40, 41, 64, 65, 66, 67, 68, 69, 70, 71,
      72, 73, 74, 75, 76, 77, 78, 79, 80, 81, 82, 83, 84
<223> OTHER INFORMATION: n = A,T,C or G
<220> FEATURE:
<223> OTHER INFORMATION: Synthetic oligonucleotide

<400> SEQUENCE: 13
tcaagtactt ctgatctaga nnnnnnnnnn nnnnnnnnnn ncctaggtta cgtactacct        60
aggnnnnnnn nnnnnnnnnn nnnntctagc tgagaagtag acag                        104

<210> SEQ ID NO 14
<211> LENGTH: 87
<212> TYPE: DNA
<213> ORGANISM: Artificial Sequence
<220> FEATURE:
<221> NAME/KEY: misc_feature
```

<222> LOCATION: 14, 15, 16, 17, 18, 19, 20, 21, 22, 23, 24, 25, 26, 27,
    28, 29, 30, 31, 32, 33, 34, 57, 58, 59, 60, 61, 62, 63, 64,
    65, 66, 67, 68, 69, 70, 71, 72, 73, 74, 75, 76, 77
<223> OTHER INFORMATION: n = A,T,C or G
<220> FEATURE:
<223> OTHER INFORMATION: Synthetic oligonucleotide

<400> SEQUENCE: 14
gaagactaga tctnnnnnnn nnnnnnnnnn nnnnggatcc aatgcatgat ggatccnnnn    60
nnnnnnnnnn nnnnnnnaga tcgactc                                      87

<210> SEQ ID NO 15
<211> LENGTH: 69
<212> TYPE: DNA
<213> ORGANISM: Artificial Sequence
<220> FEATURE:
<221> NAME/KEY: misc_feature
<222> LOCATION: 6, 7, 8, 9, 10, 11, 12, 13, 14, 15, 16, 17, 18, 19, 20,
    21, 22, 23, 24, 25, 26, 49, 50, 51, 52, 53, 54, 55, 56, 57,
    58, 59, 60, 61, 62, 63, 64, 65, 66, 67, 68, 69
<223> OTHER INFORMATION: n = A,T,C or G
<220> FEATURE:
<223> OTHER INFORMATION: Synthetic oligonucleotide

<400> SEQUENCE: 15
gatctnnnnn nnnnnnnnnn nnnnnnggat ccaatgcatg atggatccnn nnnnnnnnn    60 nnnnnnnnn                                                          69

<210> SEQ ID NO 16
<211> LENGTH: 65
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,
    17, 18, 19, 20, 21, 44, 45, 46, 47, 48, 49, 50, 51, 52, 53,
    54, 55, 56, 57, 58, 59, 60, 61, 62, 63, 64
<223> OTHER INFORMATION: n = A,T,C or G
<220> FEATURE:
<223> OTHER INFORMATION: Synthetic oligonucleotide

<400> SEQUENCE: 16
nnnnnnnnnn nnnnnnnnnn nggatccatc atgcattgga tccnnnnnnn nnnnnnnnnn    60 nnnna                                                              65

<210> SEQ ID NO 17
<211> LENGTH: 51
<212> TYPE: DNA
<213> ORGANISM: Artificial Sequence
<220> FEATURE:
<221> NAME/KEY: misc_feature
<222> LOCATION: 6, 7, 8, 9, 10, 11, 12, 13, 14, 15, 16, 17, 18, 19, 20,
    21, 22, 23, 24, 25, 32, 33, 34, 35, 36, 37, 38, 39, 40, 41,
    42, 43, 44, 45, 46, 47, 48, 49, 50, 51
<223> OTHER INFORMATION: n = A,T,C or G
<220> FEATURE:
<223> OTHER INFORMATION: Synthetic oligonucleotide

<400> SEQUENCE: 17
gatctnnnnn nnnnnnnnnn nnnnnggatc cnnnnnnnnn nnnnnnnnnn n             51

<210> SEQ ID NO 18
<211> LENGTH: 47
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,

```
      17, 18, 19, 20, 27, 28, 29, 30, 31, 32, 33, 34, 35, 36, 37,
      38, 39, 40, 41, 42, 43, 44, 45, 46
<223> OTHER INFORMATION: n = A,T,C or G
<220> FEATURE:
<223> OTHER INFORMATION: Synthetic oligonucleotide

<400> SEQUENCE: 18
nnnnnnnnnn nnnnnnnnnn ggatccnnnn nnnnnnnnnn nnnnnna                   47

<210> SEQ ID NO 19
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 19 tttttttgata tca                                                        13

<210> SEQ ID NO 20
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 20
cgcgtgatat caaaaaa                                                     17

<210> SEQ ID NO 21
<211> LENGTH: 7
<212> TYPE: DNA
<213> ORGANISM: Artificial Sequence
<220> FEATURE:
<221> NAME/KEY: misc_feature
<222> LOCATION: 7
<223> OTHER INFORMATION: n = 20 or 21 A,T,C or G
<220> FEATURE:
<223> OTHER INFORMATION: Synthetic oligonucleotide

<400> SEQUENCE: 21 gccgagn                                                                 7

<210> SEQ ID NO 22
<211> LENGTH: 7
<212> TYPE: DNA
<213> ORGANISM: Artificial Sequence
<220> FEATURE:
<221> NAME/KEY: misc_feature
<222> LOCATION: 1
<223> OTHER INFORMATION: n = 18 or 19 A,T,C or G
<220> FEATURE:
<223> OTHER INFORMATION: Synthetic oligonucleotide

<400> SEQUENCE: 22 nctcggc                                                                 7

<210> SEQ ID NO 23
<211> LENGTH: 22
<212> TYPE: DNA
<213> ORGANISM: Artificial Sequence
<220> FEATURE:
<221> NAME/KEY: misc_feature
<222> LOCATION: 7, 8, 9, 10, 11, 12, 13, 14, 15, 16, 17, 18, 19, 20,
      21, 22
<223> OTHER INFORMATION: n = A,T,C or G
<220> FEATURE:
<223> OTHER INFORMATION: Synthetic oligonucleotide
```

<400> SEQUENCE: 23
ctggagnnnn nnnnnnnnnn nn                                        22

<210> SEQ ID NO 24
<211> LENGTH: 20
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14
<223> OTHER INFORMATION: n = A,T,C or G
<220> FEATURE:
<223> OTHER INFORMATION: Synthetic oligonucleotide

<400> SEQUENCE: 24
nnnnnnnnnn nnnnctccag                                           20

<210> SEQ ID NO 25
<211> LENGTH: 17
<212> TYPE: DNA
<213> ORGANISM: Artificial Sequence
<220> FEATURE:
<221> NAME/KEY: misc_feature
<222> LOCATION: 7, 8, 9, 10, 11, 12, 13, 14, 15, 16, 17
<223> OTHER INFORMATION: n = A,T,C or G
<220> FEATURE:
<223> OTHER INFORMATION: Synthetic oligonucleotide

<400> SEQUENCE: 25
ggcggannnn nnnnnnn                                              17

<210> SEQ ID NO 26
<211> LENGTH: 15
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9
<223> OTHER INFORMATION: n = A,T,C or G
<220> FEATURE:
<223> OTHER INFORMATION: Synthetic oligonucleotide

<400> SEQUENCE: 26
nnnnnnnnnt ccgcc                                                15

<210> SEQ ID NO 27
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 27 gaactgac                                                         8

<210> SEQ ID NO 28
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 28 cttcatct                                                         8

<210> SEQ ID NO 29
<211> LENGTH: 84

```
<212> TYPE: DNA
<213> ORGANISM: Artificial Sequence
<220> FEATURE:
<221> NAME/KEY: misc_feature
<222> LOCATION: 6, 7, 8, 9, 10, 11, 12, 13, 14, 15, 16, 17, 18, 19, 20,
      21, 22, 23, 24, 25, 48, 49, 50, 51, 52, 53, 54, 55, 56, 57,
      58, 59, 60, 61, 62, 63, 64, 65, 66, 67
<223> OTHER INFORMATION: n = A,T,C or G
<220> FEATURE:
<223> OTHER INFORMATION: Synthetic oligonucleotide

<400> SEQUENCE: 29
gatctnnnnn nnnnnnnnnn nnnnnggatc caatgcatga tggatccnnn nnnnnnnnnn      60 nnnnnnntttt ttgatatcac gcgt                                            84

<210> SEQ ID NO 30
<211> LENGTH: 80
<212> TYPE: DNA
<213> ORGANISM: Artificial Sequence
<220> FEATURE:
<221> NAME/KEY: misc_feature
<222> LOCATION: 18, 19, 20, 21, 22, 23, 24, 25, 26, 27, 28, 29, 30, 31,
      32, 33, 34, 35, 36, 37, 60, 61, 62, 63, 64, 65, 66, 67, 68,
      69, 70, 71, 72, 73, 74, 75, 76, 77, 78, 79
<223> OTHER INFORMATION: n = A,T,C or G
<220> FEATURE:
<223> OTHER INFORMATION: Synthetic oligonucleotide

<400> SEQUENCE: 30
acgcgtgata tcaaaaannn nnnnnnnnnn nnnnnngga tccatcatgc attggatccn      60
nnnnnnnnnn nnnnnnnnna                                                 80

<210> SEQ ID NO 31
<211> LENGTH: 68
<212> TYPE: DNA
<213> ORGANISM: Artificial Sequence
<220> FEATURE:
<221> NAME/KEY: misc_feature
<222> LOCATION: 6, 7, 8, 9, 10, 11, 12, 13, 14, 15, 16, 17, 18, 19, 20,
      21, 22, 23, 24, 25, 32, 33, 34, 35, 36, 37, 38, 39, 40, 41,
      42, 43, 44, 45, 46, 47, 48, 49, 50, 51
<223> OTHER INFORMATION: n = A,T,C or G
<220> FEATURE:
<223> OTHER INFORMATION: Synthetic oligonucleotide

<400> SEQUENCE: 31
gatctnnnnn nnnnnnnnnn nnnnnggatc cnnnnnnnnn nnnnnnnnnn nttttttgata      60 tcacgcgt                                                               68

<210> SEQ ID NO 32
<211> LENGTH: 64
<212> TYPE: DNA
<213> ORGANISM: Artificial Sequence
<220> FEATURE:
<221> NAME/KEY: misc_feature
<222> LOCATION: 18, 19, 20, 21, 22, 23, 24, 25, 26, 27, 28, 29, 30, 31,
      32, 33, 34, 35, 36, 37, 44, 45, 46, 47, 48, 49, 50, 51, 52,
      53, 54, 55, 56, 57, 58, 59, 60, 61, 62, 63
<223> OTHER INFORMATION: n = A,T,C or G
<220> FEATURE:
<223> OTHER INFORMATION: Synthetic oligonucleotide

<400> SEQUENCE: 32
acgcgtgata tcaaaaannn nnnnnnnnnn nnnnnngga tccnnnnnnn nnnnnnnnnn      60 nnna                                                                  64
```